US006173037B1

United States Patent
Brouwer

(10) Patent No.: US 6,173,037 B1
(45) Date of Patent: Jan. 9, 2001

(54) METHOD OF AND APPARATUS FOR X-RAY FLUORESCENT ANALYSIS OF THIN LAYERS

(75) Inventor: Peter N. Brouwer, Almelo (NL)

(73) Assignee: U.S. Philips Corporation, New York, NY (US)

(*) Notice: Under 35 U.S.C. 154(b), the term of this patent shall be extended for 0 days.

(21) Appl. No.: 09/351,381

(22) Filed: Jul. 13, 1999

(30) Foreign Application Priority Data

Jul. 16, 1998 (EP) .................................................. 98202383

(51) Int. Cl.⁷ ................................................. G01N 23/223
(52) U.S. Cl. ................................................. 378/45; 378/50
(58) Field of Search .......................................... 378/45–50

(56) References Cited

FOREIGN PATENT DOCUMENTS 2706601  1/1998 (JP) .

Primary Examiner—Craig E. Church
(74) Attorney, Agent, or Firm—Tony E. Piotrowski

(57) ABSTRACT

An X-ray fluorescent method for performing measurements on a thin layer provided on a substrate, notably a silicon substrate provided with a layer of tungsten silicide ($WSi_x$). The layer thickness and the concentration of the chemical elements in the layer can be determined in known manner by measurement of the intensity of a hard and a soft X-ray line in the fluorescent radiation. In conformity with the invention, the reliability and/or the accuracy of this determination can be established by measurement of the intensity of a third X-ray line, preferably being a line whose wavelength lies between that of the first two lines. Using a minimization procedure (least squares method applied to $\chi^2$), the optimum values of c and d are determined. The accuracy of the determination can be established by variation of the optimum value of $\chi^2$.

10 Claims, 3 Drawing Sheets

METHOD OF AND APPARATUS FOR X-RAY FLUORESCENT ANALYSIS OF THIN LAYERS

FIELD OF THE INVENTION

The invention relates to a method of examining a sample by means of X-ray fluorescent analysis, which sample comprises a substrate which is provided with a thin layer and contains a first chemical element, said thin layer containing the same chemical element and a second chemical element which does not form part of the substrate, which method includes the following steps: irradiation of the sample by means of primary X-rays, measurement of the intensity of comparatively hard X-ray fluorescent radiation and of comparatively soft X-ray fluorescent radiation, both types of radiation being generated in the sample in response to the irradiation by means of the primary X-rays. The invention also relates to an apparatus for carrying out said method.

DESCRIPTION OF PRIOR ART

A method of this kind is known from Japanese patent No. 2706601. The cited Japanese patent describes an X-ray fluorescent analysis method for determining the thickness of a thin layer on a substrate and for determining the concentration of a chemical element present in said thin layer. To this end, the sample is irradiated by means of X-rays (primary radiation) emanating from an X-ray source. The sample is formed by a substrate which consists of a first chemical element, in this case being silicon, and on which there is provided a thin layer which consists of the first chemical element (i.re. silicon) and a second chemical element, in this case being tungsten. In the sample the primary radiation generates X-ray fluorescent radiation which contains characteristic radiation of the chemical elements present in the specimen, so silicon and tungsten. This characteristic radiation comprises comparatively hard X-rays (for example having a wavelength of the order of magnitude of from 0.02 to 1 nm) as well as comparatively soft X-rays (for example, having a wavelength of the order of magnitude of from 2 to 15 nm).

According to the known method the apparatus response is determined by means of known reference samples. Using the apparatus response, the layer thickness and the concentration of one of the chemical elements in the layer, for example tungsten, is determined on the basis of the measured intensities of the comparatively hard as well as the comparatively soft fluorescent radiation. Such determination is performed by means of a calculation method which is known per se for the theoretical calculation of the intensity of X-ray fluorescent radiation; this calculation method is also known as the "fundamental parameter method".

(This theoretically calculated intensity of X-ray fluorescent radiation is the intensity which occurs immediately after the radiation emanates from the sample; therefore, the effect of the entire measuring channel from the sample to the detector has not been taken into account therein.) According to the cited Japanese patent the combination of said two types of X-ray fluorescent radiation (i.e. the comparatively hard and the comparatively soft fluorescent radiation) is formed by one of the combinations of X-ray lines K with M, K with N and L with N of tungsten, or one of the combinations of X-ray lines K with M, K with N and L with N of silicon.

Even though the known method is capable of determining the thickness of the thin layer as well as the concentration of one of the chemical elements present therein, it is not capable of providing other information concerning these determinations. It is notably not possible to obtain an idea of the accuracy, and hence of the reliability, of the determinations, or to obtain an impression of a concentration gradient, if any, of one of the chemical elements present in the thin layer.

SUMMARY OF THE INVENTION

It is an object of the invention to provide a method of the kind set forth which also enables further information to be obtained in respect of the determination executed, for example the degree of accuracy of determination of the layer thickness and/or the concentration in the thin layer or a concentration gradient present in said layer.

To this end, the method according to the invention is characterized in that it also includes the following steps: measurement of the intensity of X-ray fluorescent radiation whose wavelength deviates from said comparatively hard and comparatively soft X-rays, generated in the sample in response to the irradiation by means of the primary X-rays, determination of the thickness of the thin layer and/or the concentration of the first or the second chemical element on the basis of the measured intensities of said three types of X-ray fluorescent radiation, determination of the reliability and/or the accuracy of the determination of at least one of said two quantities (thickness and concentration) on the basis of the measured intensities of said three wavelengths of the X-ray fluorescent radiation.

The invention is based on the recognition of the fact that further information as regards the determinations and/or the sample can be obtained by measurement of the intensity of at least one wavelength other than said two wavelengths. The intensity of said third wavelength can be simply derived when the equipment for measuring said two wavelengths has already been provided. Merely the calculation of the desired quantities will then require some adaptations in order to derive the additional information; this will be explained on the basis of the embodiment according to the invention.

In a further version of the method according to the invention, the wavelength of said X-ray fluorescent radiation whose wavelength deviates from said comparatively hard and comparatively soft X-rays lies between the wavelengths of said comparatively hard and comparatively soft X-rays. Consequently, in many cases it is possible to utilize the same equipment of the X-ray spectrometer, notably the analysis crystals and the X-ray detector, as used for the measurement of the intensity of the comparatively hard and the comparatively soft X-rays. Furthermore, it may be assumed that the comparatively hard X-rays contain information mainly concerning the layer thickness and that the comparatively soft X-rays contain information mainly concerning the concentration. If the third wavelength were chosen so as to have the same order of magnitude as said comparatively hard or comparatively soft X-rays, only little additional information would be obtained. As a result of said choice, therefore, it is achieved that as much additional information as possible concerning the thin layer is obtained.

The invention will be described in detail hereinafter with reference to the Figures. Therein:

DETAILED DESCRIPTION OF THE PREFERRED EMBODIMENTS

Figure 1:
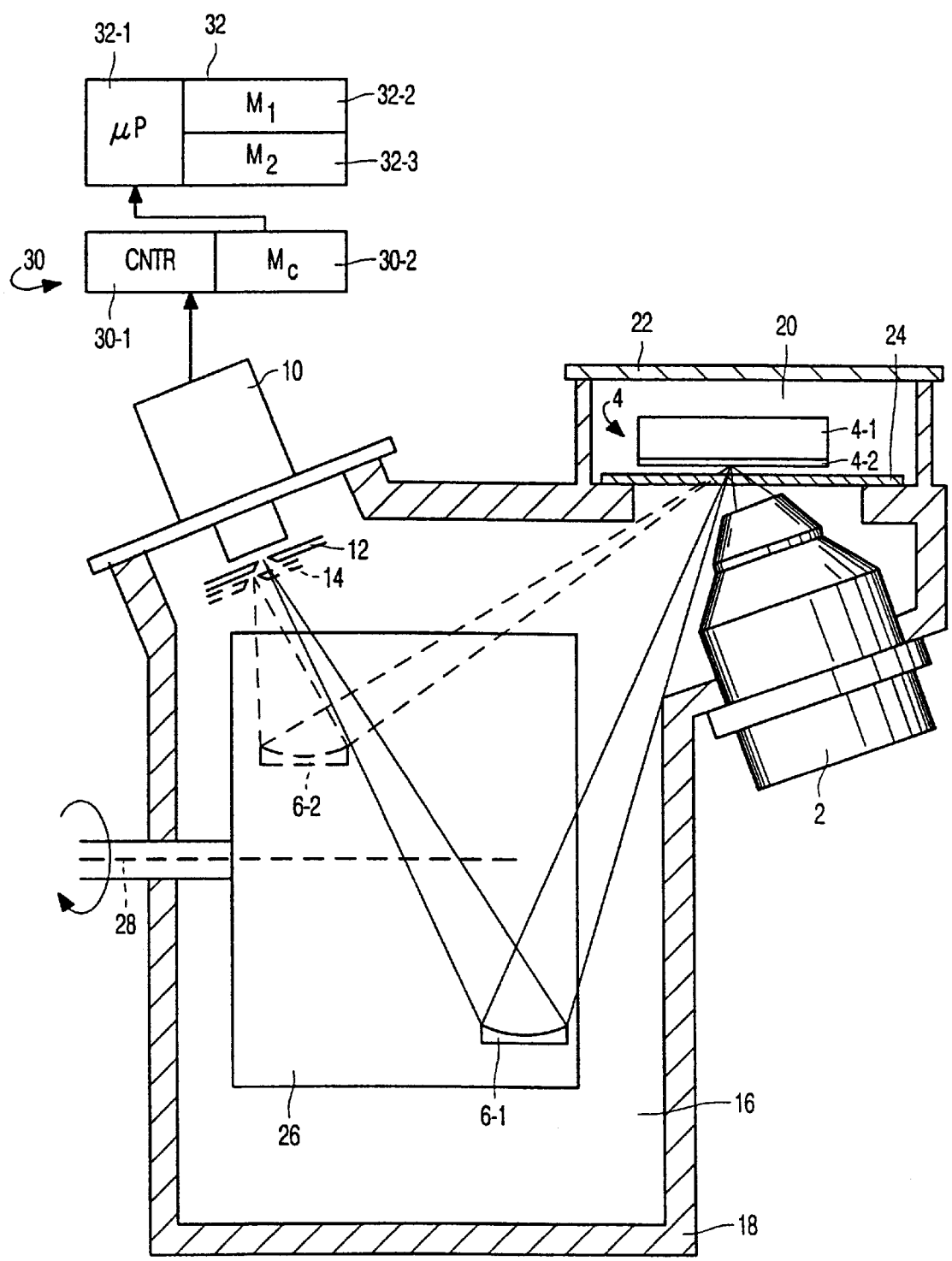
FIG. 1 shows a relevant part of an X-ray fluorescence spectrometer for carrying out the method according to the invention.

FIG. 1 shows a relevant part of an analytic X-ray apparatus in the form of an X-ray fluorescence spectrometer for carrying out the method according to the invention. The X-ray spectrometer includes an X-ray tube 2 for generating the primary X-rays for irradiating a sample 4 to be analyzed. The sample 4 consists of a substrate 4-1 which consists, for example of silicon and on which there is provided a thin layer 4-2 which consists of tungsten silicide ($WSi_x$, where x is of the order of magnitude of 2.6 so that the percentage by weight of tungsten amounts to approximately 72%). The thickness of this thin layer is of the order of magnitude of between 20 and 250 nm.

In the sample the primary X-rays generate X-ray fluorescent radiation which contains characteristic radiation of the chemical elements present in the sample, i.e. silicon and tungsten. The characteristic radiation comprises comparatively hard X-rays (for example, having a wavelength of the order of magnitude of from 0.02 to 2 nm) as well as comparatively soft X-rays (for example, having a wavelength of the order of magnitude of from 2 to 15 nm).

The X-ray fluorescent radiation emanating from the sample 4 is reflected to one or more X-ray detectors 10 by one or more analysis crystals. The X-ray detector 10 includes electronic means for converting the detected X-ray intensity into electronic counting pulses. These counting pulses are received by a counting unit 30 and transferred, by a counter 30-1, to a memory 30-2 which forms part of the counting unit 30. The assembly formed by the detector 10 and the counting unit 30 constitutes the detection unit for measuring the intensity of the wavelengths selected by the selection unit. The analysis crystals serve to select the desired wavelength from the fluorescent radiation in a manner which is known per se. The Figure shows two analysis crystals 6-1 and 6-2 which have a curved surface for a focusing X-ray optical system. However, in order to carry out the present invention these crystals may also be plane analysis crystals. The analysis crystals constitute the selection means for selecting at least the desired wavelengths from the X-ray fluorescent radiation generated in the sample. One of the analysis crystals, for example the analysis crystal 6-1, is arranged to select the comparatively hard fluorescent radiation; for example an LiF crystal which is known per se can be used for this purpose. The other analysis crystal 6-2 is then arranged to select the comparatively soft fluorescent radiation; for example, a known X-ray multilayer mirror can be used for this purpose.

It is not of essential importance to the invention whether the fluorescent radiation is simultaneously reflected to a respective detector associated with each crystal by both analysis crystals, or whether the analysis crystals are consecutively arranged in the fluorescent radiation beam. When the analysis crystals are simultaneously irradiated, two detectors must be used simultaneously so as to enable separate measurement of the intensities of the hard and the soft fluorescent radiation. In that case the beams reflected by each of the analysis crystals should be separated in space so that each detector can separately measure the intensity associated with the relevant analysis crystal. In the case of consecutive irradiation of the analysis crystals it is also necessary to use two detectors; however, these detectors can then be consecutively arranged in the location of the detector 10 shown in the Figure. For the hard fluorescent radiation a detector in the form of a known scintillation counter is then used, whereas a so-called flow-counter is used as the detector for the soft fluorescent radiation.

It has been assumed for FIG. 1 that the analysis crystals 6-1 and 6-2 are consecutively irradiated. In that case the analysis crystals are mounted on a changer in the form of a wheel 26. The analysis crystals can thus be arranged, with the correct orientation and in the correct location, in the beam of fluorescent radiation emanating from the sample 4. The wheel 26 is rotatable about a shaft 28 so that it can be driven from outside the measuring space so as to be moved to a desired position. It is also possible to provide the detector collimation slits 12 and 14, associated with each of the analysis crystals 6-1 and 6-2, respectively, on the changer in the form of the wheel. As a result, the detector is automatically provided with the correct collimation slit when an analysis crystal is changed. The X-rays reflected by the analysis crystal 6-1 reach the detector 10 via a detector collimation slit 12.

The beam path from the X-ray tube to the detector extends in a measuring space 16 which can be hermetically sealed; the sample 4 may be arranged in a sample space 20 which is separate from the measuring space and which can be isolated from the measuring space 16 by means of a valve 24. The space 16 is enclosed by a housing 18. The separate sample space includes its own entrance 22. The measuring space can thus be conditioned (for example, evacuated, filled with a desired gas or adjusting to a desired temperature) in the manner imposed by the measurement to be executed. If the sample is to be changed, the valve 24 is closed so that the entire measuring space need not come into contact with the ambient atmosphere. The sample is changed via the entrance 22 and only the (much smaller) sample space need subsequently be adapted to the measuring conditions again.

The measurement of the intensity of the X-ray fluorescent radiation whose wavelength deviates from said comparatively hard and comparatively soft X-rays (to be referred to hereinafter as the fluorescent radiation of mean hardness) is performed in the same way as that used to measure the hard and the soft fluorescent radiation. The choice as to which of the two analysis crystals and which type of X-ray detector is used is dependent on the wavelength of the fluorescent radiation of mean hardness. If desired, a separate analysis crystal and/or a separate X-ray detector may also be used for the latter fluorescent radiation.

The measurements to be carried out according to the invention are performed by irradiating the sample by means of the primary X-rays. The analysis crystal associated with the wavelength of the fluorescent radiation to be observed is arranged in the beam path between the sample 4 and the detector 10. When the detection unit 10, 30 has detected the number of counting pulses during the specified period of time, the same procedure is repeated for the other two wavelengths of interest. The intensity of the fluorescent radiation is thus determined for each of the three wavelengths. Hereinafter, the determination, on the basis of the intensities thus measured, of the thickness of the thin layer 4-2, the concentration of the desired chemical element in the thin layer, and the uncertainty in the two quantities will be described with reference to the FIGS. 2 and 3. Processor means 32, connected to the detection unit, are provided so as to execute the calculations. The processor means consist of a microprocessor 32-1 and two memory fields 32-3 and 32-3 co-operating therewith. The memory field 32-2 is used, for example for the storage of the intensities received from the memory 30-2 and represented by the number of counting pulses associated with a given measurement. This memory field can also be used to store intermediate results and final results of the calculations. The memory field 32-3 is used, for example for the storage of the programs to be executed by the microprocessor.

Figure 2:
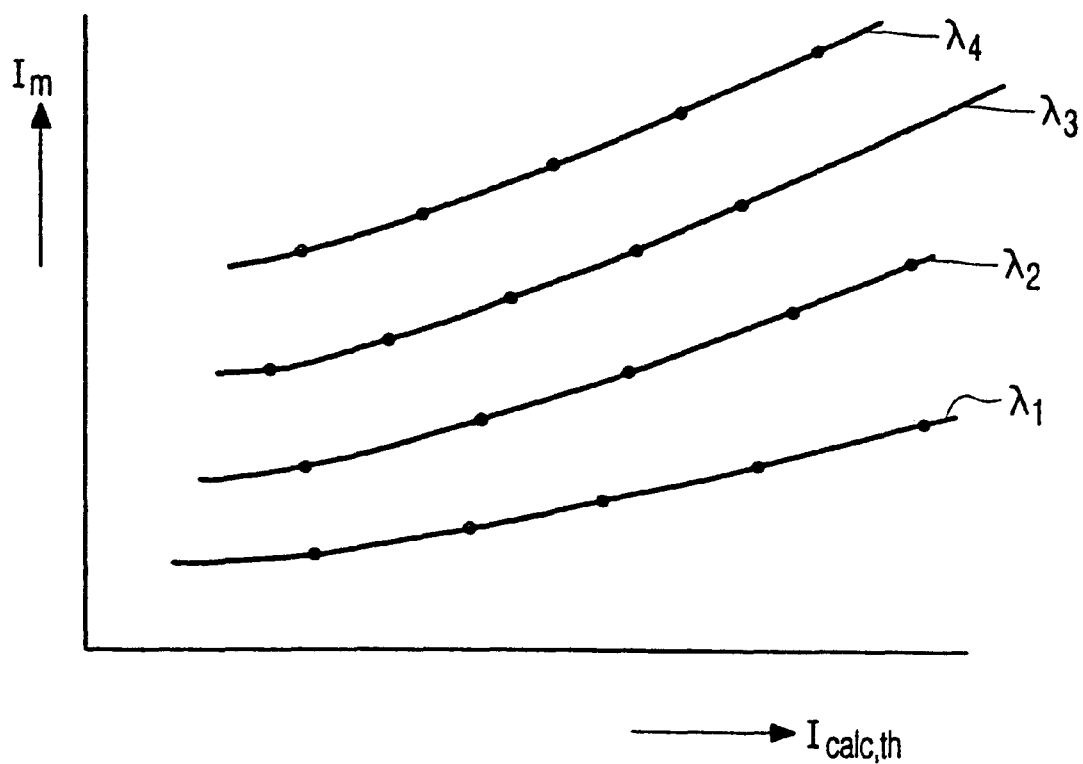
FIG. 2 shows an example of a number of calibration curves which represent the apparatus response and are required so as to carry out the calculations according to the invention.

FIG. 2 shows a number of curves (the calibration curves representing the apparatus response) which represent the relationship between theoretically calculated fluorescence intensities and associated measured fluorescence intensities.

When a known sample (i.e. a sample of known composition and magnitude) is irradiated by means of a known X-ray source (i.e. a source whose spectral composition is fully known), the intensity of a given wavelength of the fluorescent radiation can be calculated. The algorithm for this calculation is generally known as the "fundamental parameter method". The intensity thus calculated will be referred to hereinafter as the calculated theoretical intensity $I_{calc,th}$. The latter quantity, therefore, will have different values for the various wavelengths. On the one hand a number of samples of known, different composition can be taken (the reference samples) so as to determine the theoretical intensity $I_{calc,th}$ of these samples for different wavelengths. On the other hand, these samples can be subjected to measurements in conformity with the invention so that the intensity at said wavelengths is measured. Therefore, this intensity will be referred to as the measured intensity $I_m$. For each sample the calculated theoretical intensity $I_{calc,th}$ and also the measured intensity $I_m$ is thus determined for each of said wavelengths. Consequently, a (for example, graphic) relationship can be established between $I_{calc,th}$ and $I_m$ for each of said wavelengths of the fluorescent radiation. This relationship will be referred to hereinafter as a calibration curve. FIG. 2 shows, by way of example, four of such calibration curves, so for four different wavelengths $\lambda_1$ to $\lambda_4$, each curve comprising five calculated and measured calibration points. The calibration curves are used to determine the thickness of the thin layer 4-2, the concentration of the desired chemical element, and the uncertainties in these quantities. The method of execution will be described in detail hereinafter with reference to the flow chart of FIG. 3.

Figure 3:
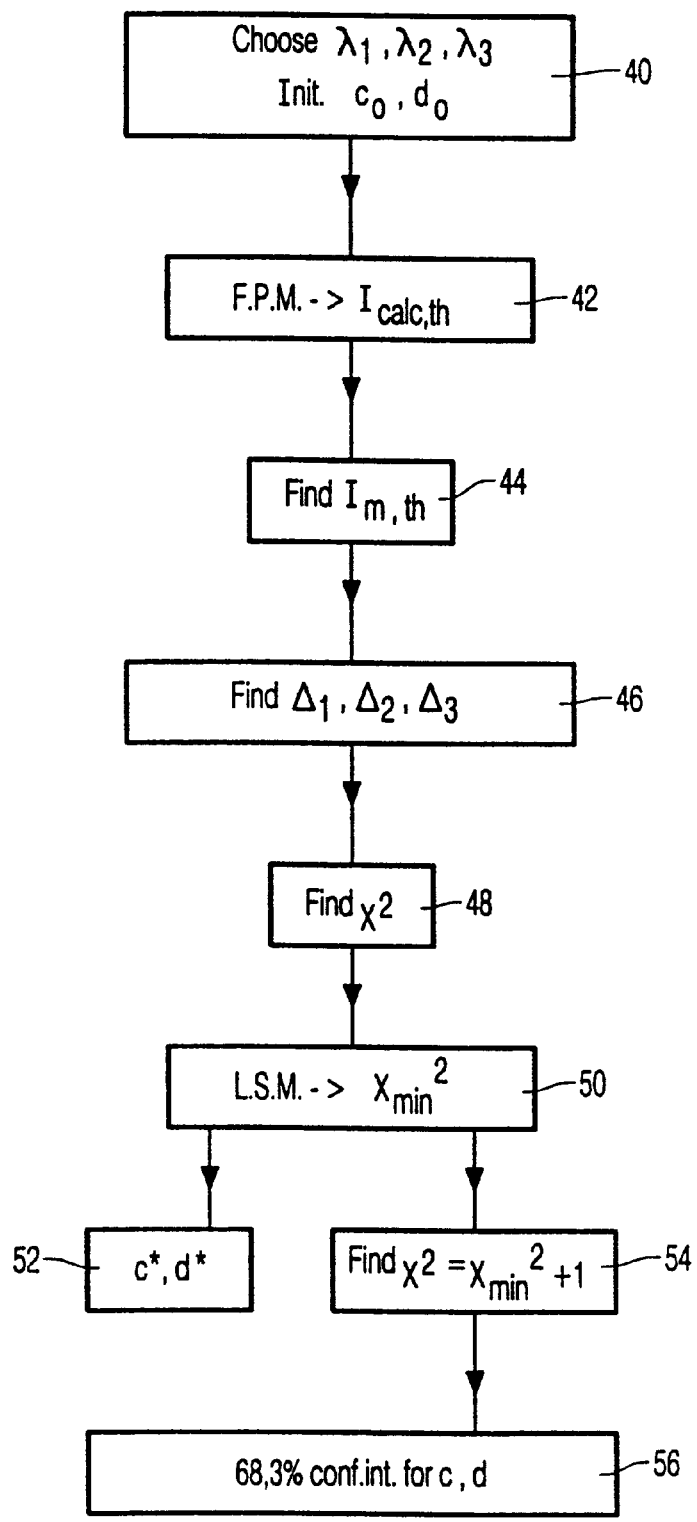
FIG. 3 shows a flow chart representing the calculations according to the invention.

FIG. 3 shows a flow chart illustrating the calculations according to the invention. For the execution of these calculations it is assumed that the measured intensities $I_m$ (so three numbers in case of determination of the intensity of three X-ray lines) are known.

The calculation is started by entering the three values $\lambda_1$, $\lambda_2$ and $\lambda_3$ of the wavelengths of the three measured X-ray lines and the assumption of arbitrary initial values $c_0$ and $d_0$ for the concentration to be calculated for the chemical element of interest in the thin layer and the thickness to be calculated for the thin layer (block 40), respectively. Using this information, the algorithm of the fundamental parameter method (F.P.M., block 42) can be applied so as to execute a calculation for the determination of three values of the calculated theoretical intensity $I_{calc,th}$, i.e. one for each of the three wavelengths.

Subsequently, using the calibration curves associated with the spectrometer configuration, the associated calculated measured intensity $I_{m,th}$ is derived (block 44) from the calculated theoretical intensity $I_{calc,th}$. It is to be noted that the calculated measured values do not represent the actually measured intensities, but the intensities which, in conformity with the FPM algorithm, would be measured for the given wavelengths on a sample while using the assumed initial values $c_0$ and $d_0$.

The three values thus found for $I_{m,th}$ can then be compared with the three actually measured values $I_m$ (block 46). During this step of the calculation the difference $\Delta = I_{m,th} - I_m$ is determined for each of the three wavelengths, so that this step yields three values $\Delta_1$, $\Delta_2$ and $\Delta_3$. The latter three values can be used to determine a quantity $\chi^2$ in conformity with the relation $\chi^2 = \Delta_1^2 + \Delta_2^2 + \Delta_3^2$ (block 48). (In conformity with the theory of the $\chi^2$ test ("$\chi$-square test") which is known per se for mathematical statistics, said sum of squared deviations should still be divided by the number of degrees of freedom. In the present case, involving three wavelengths and two parameters c and d, the number of degrees of freedom equals 1, so that this amount is omitted.) In conformity with the theory of the $\chi^2$ test, for $\chi^2 = 1$ the values assumed for the concentration c and the thickness d are equal to the actual values of c and d. Generally this will not be the case for the assumed arbitrary initial values $c_0$ and $d_0$. Therefore, the calculation includes an algorithm for varying the values of c and d in such a manner that $\chi^2$ is minimized (block 50); this is because in that case optimum correspondence exists between the actual values of c and d and the values of c and d occurring in the calculation in that situation, said values being denoted by the references c* and d*. Said minimization algorithm, called the Least Squares Method or LSM, is generally known. The result of the latter algorithm is formed by the values searched for the concentration c* and the thickness d* (block 52).

In conformity with the invention a measure of the reliability and/or the accuracy of c* and d* can now also be determined. A first impression in respect of the reliability is already obtained from the value of $\chi^2$ (denoted as $\chi_{min}^2$) associated with the values of c* and d*. As has already been stated, statistically speaking this value equals 1 in the case of exact correspondence between the calculated c* and d* and the actual c and d. ("Statistically speaking" is to be understood to mean that the mean value of $\chi^2$ approximates 1 when the experiment is repeated many times). If the final value $\chi_{min}^2$ does not excessively deviate from 1, an indication is already obtained that the above calculation process constitutes a suitable representation of the physical process. A more numerical impression of the accuracy achieved can be obtained by incrementing the final value $\chi_{min}^2$ by a given amount and by determining the set of values of c and d associated with said incremented value. Evidently, the larger the amount whereby $\chi_{min}^2$ is incremented, the larger the associated values of c and d will be. The value 1 is customarily used for the $\chi^2$ test, corresponding to a 68% confidence interval for the associated c and d values (block 56). (In conformity with the $\chi^2$ test theory, an increase by a value 2 would correspond to a 95% confidence interval.)

With respect to the comparison of the calculated values of the intensities and the measured values it is to be noted that it is not necessary to follow the procedure described with reference to block 44. This is because it is alternatively possible to determine from the actually measured intensities $I_m$ in the calibration curves the associated values for theoretical intensities. The latter values could then be compared with the values for $I_{calc,th}$ as determined in conformity with the block 42.

What is claimed is:

1. A method of examining a sample by means of X-ray fluorescent analysis, which sample comprises a substrate which is provided with a thin layer, the substrate containing a first chemical element, the thin layer containing the same chemical element and a second chemical element which does not form part of the substrate, said method including the steps of:

irradiating the sample by means of primary X-rays;
measuring an intensity of comparatively hard X-ray fluorescent radiation and of comparatively soft X-ray fluorescent radiation, both types of radiation being generated in the sample in response to the irradiation by means of the primary X-rays;

measuring an intensity of X-ray fluorescent radiation whose wavelength deviates from the comparatively hard and comparatively soft X-rays, generated in the sample in response to the irradiation by means of the primary X-rays, determining a thickness of the thin layer or the concentration of the first or the second chemical element on the basis of the measured intensities of the three types of X-ray fluorescent radiation, determining a reliability or an accuracy of the the thickness or the concentration determined in said determining stop on the basis of the measured intensities of the three wavelengths of the X-ray fluorescent radiation.

2. A method as claimed in claim 1, wherein the wavelength of the X-ray fluorescent radiation whose wavelength deviates from the comparatively hard and comparatively soft X-rays lies between the wavelengths of the comparatively hard and comparatively soft X-rays.

3. A method as claimed in claim 1, wherein the first chemical element is silicon.

4. A method as claimed in claim 1, wherein the second chemical element is tungsten.

5. A method as claimed in claim 4, wherein the comparatively hard, the comparatively soft and the intermediate X-ray fluorescent radiation originate from tungsten.

6. An apparatus for carrying out the method claimed in claim 1, comprising:

a sample holder for receiving the sample to be analyzed;

an X-ray source for producing the primary X-rays;

selection means for selecting at least two desired wavelengths from the X-ray fluorescent radiation generated in the sample;

a detection unit for measuring the intensity of the wavelengths selected by the selection means, wherein said selection means includes means for selecting a third desired wavelength from the X-ray fluorescent radiation generated in the sample, the third wavelength being different from the two desired wavelengths, and wherein said detection unit includes means for measuring an intensity of the third wavelength, said apparatus also includes processor means for determining the thickness of the thin layer or the concentration of the first or the second chemical element on the basis of the measured intensities of the three types of X-ray fluorescent radiation, and for determining the reliability or the accuracy of the the thickness or the concentration on the basis of the measured intensities of the three wavelengths of the X-ray fluorescent radiation.

7. An apparatus as claimed in claim 6, wherein the wavelength of the X-ray fluorescent radiation whose wavelength deviates from the comparatively hard and comparatively soft X-rays lies between the wavelengths of the comparatively hard and comparatively soft X-rays.

8. An apparatus as claimed in claim 6, wherein the first chemical element is silicon.

9. An apparatus as claimed in claim 6, wherein the second chemical element is tungsten.

10. An apparatus as claimed in claim 9, wherein the comparatively hard, the comparatively soft and the intermediate X-ray fluorescent radiation originate from tungsten.

* * * * *